(12) United States Patent
Lucke et al.

(10) Patent No.: US 12,064,622 B2
(45) Date of Patent: Aug. 20, 2024

(54) MEDICAL DEVICES FOR ABLATING TISSUE

(71) Applicant: MINNETRONIX, INC., St. Paul, MN (US)

(72) Inventors: Lori Lucke, Rosemount, MN (US); Vlad Bluvshtein, Plymouth, MN (US); Daniel Friedrichs, Mendota Heights, MN (US)

(73) Assignee: MINNETRONIX, INC., St. Paul, MN (US)

( * ) Notice: Subject to any disclaimer, the term of this patent is extended or adjusted under 35 U.S.C. 154(b) by 426 days.

(21) Appl. No.: 16/369,947

(22) Filed: Mar. 29, 2019

(65) Prior Publication Data

US 2019/0298994 A1     Oct. 3, 2019

Related U.S. Application Data

(60) Provisional application No. 62/650,748, filed on Mar. 30, 2018.

(51) Int. Cl.
*A61B 18/14* (2006.01)
*A61B 18/12* (2006.01)
(Continued)

(52) U.S. Cl.
CPC ............ *A61N 1/06* (2013.01); *A61B 18/1206* (2013.01); *A61B 18/14* (2013.01); *A61N 1/40* (2013.01);
(Continued)

(58) Field of Classification Search
CPC .. A61N 1/06; A61N 1/40; A61B 18/14; A61B 18/1206; A61B 2018/00577;
(Continued)

(56) References Cited

U.S. PATENT DOCUMENTS

| 4,785,829 A | 11/1988 | Convert et al. |
| 4,940,933 A | 7/1990 | Jenkins |

(Continued)

FOREIGN PATENT DOCUMENTS

| EP | 1862137 A1 | 5/2007 |
| EP | 2030584 A1 | 3/2009 |

(Continued)

OTHER PUBLICATIONS

Dodd et al, "Radiofrequency Thermal Ablation: Computer Analysis of the Size of the Thermal Injury Created by Overlapping Ablations," AJR, 177:777-782, Oct. 2001.
(Continued)

*Primary Examiner* — Eun Hwa Kim
*Assistant Examiner* — Catherine C. Premraj
(74) *Attorney, Agent, or Firm* — Seager, Tufte & Wickhem, LLP

(57) ABSTRACT

Devices and methods for ablating tissue are disclosed. A method for ablating tissue includes applying a first radio frequency ablation current to a target tissue and applying a second radio frequency ablation current to the target tissue. Additionally, the ratio of the frequency of the first radio frequency ablation current to the second radio frequency ablation current is in the range of 1:2 to 1:400.

25 Claims, 6 Drawing Sheets

(51) Int. Cl.
*A61N 1/06* (2006.01)
*A61N 1/40* (2006.01)
*A61B 18/00* (2006.01)

(52) U.S. Cl.
CPC .............. *A61B 2018/00577* (2013.01); *A61B 2018/00791* (2013.01); *A61B 2018/00827* (2013.01); *A61B 2018/00875* (2013.01); *A61B 2018/00892* (2013.01); *A61B 2018/1253* (2013.01); *A61B 2018/126* (2013.01); *A61B 2018/128* (2013.01)

(58) Field of Classification Search
CPC ........... A61B 2018/00791; A61B 2018/00827; A61B 2018/00875; A61B 2018/00892; A61B 2018/1253; A61B 2018/126; A61B 2018/128
See application file for complete search history.

(56) References Cited

U.S. PATENT DOCUMENTS

| | | | |
|---|---|---|---|
| 5,542,916 A * | 8/1996 | Hirsch | A61B 18/1815 604/22 |
| 5,620,481 A | 4/1997 | Desai et al. | |
| 6,309,386 B1 | 10/2001 | Bek | |
| 6,730,078 B2 | 5/2004 | Simpson et al. | |
| 7,305,311 B2 | 12/2007 | van Zyl | |
| 7,344,533 B2 | 3/2008 | Pearson et al. | |
| 7,651,492 B2 | 1/2010 | Wham | |
| 8,486,061 B2 | 7/2013 | Podhajsky | |
| 8,512,332 B2 | 8/2013 | Collins et al. | |
| 8,523,855 B2 | 9/2013 | Keppel | |
| 8,556,890 B2 | 10/2013 | Wham | |
| 8,771,269 B2 | 7/2014 | Sherman et al. | |
| 9,005,193 B2 | 4/2015 | Govari et al. | |
| 9,037,259 B2 | 5/2015 | Mathur | |
| 9,108,052 B2 | 8/2015 | Jarrard | |
| 9,113,900 B2 | 8/2015 | Buysse et al. | |
| 9,271,790 B2 | 3/2016 | Collins et al. | |
| 9,277,955 B2 | 3/2016 | Herscher et al. | |
| 9,297,845 B2 | 3/2016 | Mathur | |
| 9,649,148 B2 | 5/2017 | Woloszko et al. | |
| 2003/0073990 A1 | 4/2003 | Goble et al. | |
| 2003/0163123 A1 | 8/2003 | Goble et al. | |
| 2003/0199862 A1 * | 10/2003 | Simpson | A61B 18/1492 606/34 |
| 2005/0165390 A1 | 7/2005 | Mauti et al. | |
| 2005/0251233 A1 | 11/2005 | Kanzius | |
| 2008/0119919 A1 * | 5/2008 | Atalar | A61B 18/14 607/116 |
| 2008/0125772 A1 | 5/2008 | Stone et al. | |
| 2010/0049186 A1 | 2/2010 | Ingle et al. | |
| 2012/0029500 A1 | 2/2012 | Jenson | |
| 2012/0116387 A1 * | 5/2012 | Govari | A61B 18/1206 606/41 |
| 2013/0165924 A1 | 6/2013 | Mathur et al. | |
| 2013/0172878 A1 * | 7/2013 | Smith | A61B 18/1492 606/41 |
| 2016/0163312 A1 | 6/2016 | Henton et al. | |
| 2016/0374752 A1 | 12/2016 | Hancock et al. | |
| 2019/0201089 A1 * | 7/2019 | Waldstreicher | A61B 18/1492 |
| 2019/0247108 A1 * | 8/2019 | Levin | A61B 18/1492 |

FOREIGN PATENT DOCUMENTS

| | | |
|---|---|---|
| EP | 2939626 A1 | 4/2015 |
| WO | 0015130 A2 | 3/2000 |
| WO | 0219932 A1 | 3/2002 |
| WO | 2015085162 A1 | 6/2015 |

OTHER PUBLICATIONS

Haemmerich, "Biophysics of Radiophysics Ablation", Critical Reviews in Biomedical Engineering, 38(1): 53-63, Jan. 2010.

Choi et al, "Overlapping Ablation Using a Coaxial Radiofrequency Electrode and Multiple Cannulae System: Experimental Study in ex-Vivo Bovine Liver", Korean Journal of Radiology, 4(2): 117-123, Jun. 2003.

Haemmerich et al, "Hepatic radiofrequency ablation at low frequencies preferentially heats tumour tissue", International Journal of Hyperthermia, 22(7):563-574, Nov. 2006.

International Search Report and Written Opinion dated Jul. 22, 2019 for International Application No. PCT/US2019/024883.

* cited by examiner

MEDICAL DEVICES FOR ABLATING TISSUE

CROSS-REFERENCE TO RELATED APPLICATIONS

This application claims priority under 35 U.S.C. § 119 to U.S. Provisional Application Ser. No. 62/650,748, filed Mar. 30, 2018, the entirety of which is incorporated herein by reference.

TECHNICAL FIELD

The present disclosure pertains to medical devices, and methods for using medical devices. More particularly, the present disclosure pertains to medical devices and methods for ablating tissue.

BACKGROUND

A wide variety of medical devices and methods have been developed for medical use. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A method for ablating tissue includes applying a first radio frequency ablation current to a target tissue and applying a second radio frequency ablation current to the target tissue. Additionally, the ratio of the frequency of the first radio frequency ablation current to the second radio frequency ablation current is in the range of 1:2 to 1:400.

Alternatively or additionally to any of the embodiments above, wherein the first radio frequency ablation current and the second radio frequency ablation current are applied simultaneously to the target tissue.

Alternatively or additionally to any of the embodiments above, wherein the first radio frequency ablation current and the second radio frequency ablation current are applied in sequence to the target tissue.

Alternatively or additionally to any of the embodiments above, wherein the first radio frequency ablation current is in the range of 50 kHz to 550 kHz.

Alternatively or additionally to any of the embodiments above, wherein the second radio frequency ablation current is in the range of 600 kHz to 10,000 kHz.

Alternatively or additionally to any of the embodiments above, wherein the first radio frequency ablation current is configured to directly heat extracellular matter, and wherein the second radio frequency ablation current is configured to directly heat intracellular matter, or wherein the first radio frequency ablation current is configured to directly heat through a first current path, and wherein the second radio frequency ablation current is configured to directly heat through a second current path.

Alternatively or additionally to any of the embodiments above, wherein the first radio frequency ablation current and the second radio frequency ablation current are configured to maximize the total volume of target tissue to be ablated.

Alternatively or additionally to any of the embodiments above, wherein the first radio frequency ablation current is applied over a first time period at a first power level and the second radio frequency is applied over a second time period at a second power level, and wherein each of the first power level and the second power level are sufficiently high to ablate the target tissue site.

Alternatively or additionally to any of the embodiments above, wherein the first time period is different from the second time period.

Alternatively or additionally to any of the embodiments above, wherein at least a portion of the first time period overlaps with at least a portion of the second time period.

Alternatively or additionally to any of the embodiments above, wherein the second time period occurs immediately after the first time period.

Alternatively or additionally to any of the embodiments above, wherein the entire second time period occurs simultaneously within the first time period.

Alternatively or additionally to any of the embodiments above, wherein the first radio frequency ablation current and the second radio frequency ablation current are emitted from the same electrode source.

Alternatively or additionally to any of the embodiments above, wherein the first radio frequency ablation current and the second radio frequency ablation current are transmitted along the same electrical pathway.

Alternatively or additionally to any of the embodiments above, wherein the first radio frequency ablation current and the second radio frequency ablation current are generated between a first electrode and a second electrode, and wherein the first electrode and the second electrode operate in a monopolar arrangement.

Alternatively or additionally to any of the embodiments above, wherein the first radio frequency ablation current and the second radio frequency ablation current are generated between a first electrode and a second electrode, and wherein the first electrode and the second electrode operate in a bipolar arrangement.

Another method for ablating tissue includes applying a first radio frequency ablation current to a target tissue site through an electrode and applying a second radio frequency ablation current to the target tissue site through an electrode. Additionally, the first radio frequency ablation current has a higher frequency than the second radio frequency ablation current.

Alternatively or additionally to any of the embodiments above, wherein the first radio frequency ablation current and the second radio frequency ablation current are applied simultaneously to the target tissue site.

Alternatively or additionally to any of the embodiments above, wherein the first radio frequency ablation current and the second radio frequency ablation current are applied in sequence to the target tissue site.

Alternatively or additionally to any of the embodiments above, wherein the first radio frequency ablation current is in the range of 50 kHz to 550 kHz.

Alternatively or additionally to any of the embodiments above, wherein the second radio frequency ablation current is in the range of 600 kHz to 10,000 kHz.

Alternatively or additionally to any of the embodiments above, wherein the first radio frequency ablation current is configured to target extracellular matter, and wherein the second radio frequency ablation current is configured to target intracellular matter, or wherein the first radio frequency ablation current is configured to directly heat through a first current path, and wherein the second radio frequency ablation current is configured to directly heat through a second current path.

Alternatively or additionally to any of the embodiments above, wherein the first radio frequency ablation current and the second radio frequency ablation current are configured to maximize the total volume of target tissue to be ablated.

Alternatively or additionally to any of the embodiments above, wherein the first radio frequency ablation current is applied over a first time period at a first power level and the second radio frequency is applied over a second time period at a second power level, and wherein each of the first power level and the second power level are sufficiently high to ablate the target tissue site.

Alternatively or additionally to any of the embodiments above, wherein the first time period is different from the second time period.

Alternatively or additionally to any of the embodiments above, wherein at least a portion of the first time period overlaps with at least a portion of the second time period.

Alternatively or additionally to any of the embodiments above, wherein the second time period occurs immediately after the first time period.

Alternatively or additionally to any of the embodiments above, wherein the entire second time period occurs simultaneously within the first time period.

A medical device for ablating tissue includes a radio frequency generator configured to provide a first radio frequency ablation current to a target tissue and a second radio frequency ablation current to the target tissue. Additionally, the ratio of the frequency of the first radio frequency ablation current to the second radio frequency ablation current is in the range of 1:2 to 1:400.

Alternatively or additionally to any of the embodiments above, wherein the device is configured to apply the first radio frequency ablation current and the second radio frequency ablation current simultaneously to the target tissue.

Alternatively or additionally to any of the embodiments above, wherein the first radio frequency ablation current is in the range of 50 kHz to 550 kHz.

Alternatively or additionally to any of the embodiments above, wherein the second radio frequency ablation current is in the range of 600 kHz to 10,000 kHz. Alternatively or additionally to any of the embodiments above, wherein the first radio frequency ablation current is configured to target extracellular matter, and wherein the second radio frequency ablation current is configured to target intracellular matter, or wherein the first radio frequency ablation current is configured to directly heat through a first current path, and wherein the second radio frequency ablation current is configured to directly heat through a second current path.

A method for ablating tissue includes applying to a target tissue a first radio frequency current having a frequency at or above 1 MHz and applying to the target tissue a second radio frequency current having a frequency at or above 1 MHz and that has a frequency different from the frequency of the first radio frequency current such that the second radio frequency current interferes with the first radio frequency current to generate an interferential ablation current within the target tissue.

Alternatively or additionally to any of the embodiments above, wherein the first radio frequency current includes a frequency in the range of 1 MHz to 20 MHz.

Alternatively or additionally to any of the embodiments above, wherein the second radio frequency current includes a frequency in the range of 1 MHz to 20 MHz. Alternatively or additionally to any of the embodiments above, wherein the generated interferential ablation current includes a frequency in the range of 50 kHz to 1 MHz.

Alternatively or additionally to any of the embodiments above, wherein the generated interferential ablation current has a frequency that equals the difference between the frequency of the first radio frequency current and frequency of the second radiofrequency current.

Alternatively or additionally to any of the embodiments above, wherein the first radio frequency current is applied through a first set of electrodes, and the second radio frequency current is applied through a second set of electrodes spaced from the first set of electrodes.

Alternatively or additionally to any of the embodiments above, wherein the first radio frequency current flows along a first electrical pathway, and the second radio frequency current flows along a second electrical pathway different from the first pathway, wherein the first pathway and second pathway interfere to generate the interferential ablation current in the target tissue.

A device for ablating tissue includes a radio frequency generator configured to apply a first radio frequency current having a frequency at or above 1 MHz to a target tissue and apply a second radio frequency current having a frequency at or above 1 MHz that is different from the frequency of the first radio frequency current to the target tissue such that the second radio frequency current interferes with the first radio frequency current to generate an interferential ablation current within the target tissue.

Alternatively or additionally to any of the embodiments above, wherein the first radio frequency current includes a frequency in the range of 1 MHz to 20 MHz.

Alternatively or additionally to any of the embodiments above, wherein the second radio frequency current includes a frequency in the range of 1 MHz to 20 MHz.

Alternatively or additionally to any of the embodiments above, wherein the generated interferential ablation current includes a frequency in the range of 50 kHz to 1 MHz.

Alternatively or additionally to any of the embodiments above, wherein the generated interferential ablation current has a frequency that equals the difference between the frequency of the first radio frequency current and frequency of the second radiofrequency current.

Alternatively or additionally to any of the embodiments above, wherein the first radio frequency current is applied through a first set of electrodes, and the second radio frequency current is applied through a second set of electrodes spaced from the first set of electrodes.

Alternatively or additionally to any of the embodiments above, wherein the first radio frequency current flows along a first electrical pathway, and the second radio frequency current flows along a second electrical pathway different from the first pathway, wherein the first pathway and second pathway interfere to generate the interferential ablation current in the target tissue.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
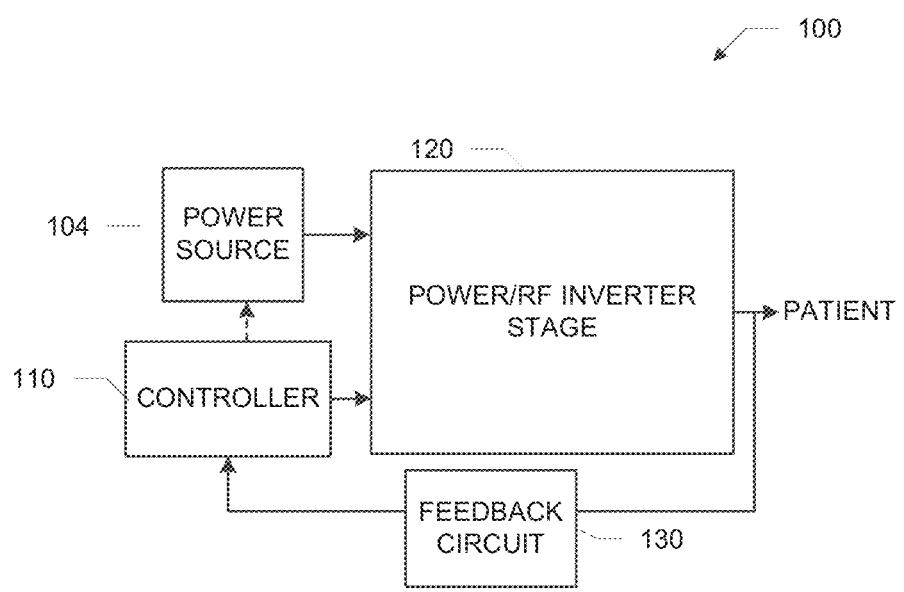
FIG. 1 is a block diagram of an example medical device according to embodiments of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of conditions exist which are effectively treated through ablation of tissue, such as damaged or disordered tissue. For instance, encapsulated tumors are often definitively treated by heating, cooling, or chemically denaturing tumorous cells until cell death occurs. These are examples of a process known as "ablation."

The types of disorders which can be treated with ablation are varied. For example, tumor ablation is a significant application, but ablation is also used to treat chronic pain through the ablation of receptor nerves. Pain in the lumbar or cervical spine and pain in the temporomandibular joint (TMJ) is often treated with ablation, offering non-analgesic pain relief that is moderately long-lasting and can be repeated if nerve regrowth occurs. Increasing aversion to opioid treatments for chronic pain has rendered nerve ablation for chronic pain a topic of considerable interest. Additionally, cardiac ablation may be performed to treat abnormal cardiac arrhythmias.

Ablation technologies take several forms. For example, injection of liquid ethanol can denature cells, but is less effective on nerve fibers. Use of cryogenic liquids to freeze cells (which causes expansion of intracellular water and bursting of cell walls) is also possible, although difficult to control and cumbersome. Most commonly, ablation is affected via heating. As heat is applied to cells, intracellular water boils and ruptures cell walls, and proteins are thermally denatured. Applying heat to an ablation target is usually accomplished using a radiofrequency (RF) electrical current. In RF ablation, an electrical current is passed via one or more pairs of electrodes through the tissue to be ablated. While the electrical oscillatory frequency of this current is sufficiently high to avoid undesirable stimulation of skeletal muscles, the current may cause heating as it passes through tissue (which is electrically resistive). In the same manner that an electric stovetop heats by passing electrical current through a resistive heating element, RF ablation heats by passing an RF current through resistive tissue.

A typical RF ablation procedure involves a surgeon positioning one or more electrodes (e.g., a needle, catheter) into (or adjacent) an ablation target tissue site, potentially using ultrasound or fluoroscopic imaging guidance. The one or more electrodes may be connected to an RF power supply and the electrical circuit completed via a large return electrode plate positioned on the patient. RF current may be allowed to flow for a length of time, after which it is assumed that sufficient heating has occurred to ablate the target tissue site. While some RF ablation systems contain temperature sensors and control systems to regulate temperature at the ablation target to a prescribed value, it is generally difficult to assess efficacy of the ablation in real-time. Practitioners rely on "recipes" for time and temperature which have previously been shown to be effective in particular clinical situations.

The design considerations of RF ablation systems may generally include at least response times and accuracy (of power delivery or temperature measurement), adaptability to different therapies, size, complexity, safety, and cost. This disclosure proposes two general examples which improve RF ablation systems related to these design considerations: inferential heating and multi-frequency heating.

FIG. 1 depicts an example medical device 100 according to an embodiment of the disclosure. The term medical device as used in this disclosure may reference any medical device designed to control power, voltage, current, temperature, impedance, energy delivered, combinations thereof (or any other similar parameter) to perform a procedure or therapy on a patient. The medical device 100 may include a controller 110, a power system (e.g., an RF generator) 120, and a feedback circuit 130. The power/RF generator 120 may receive power from a power source 104. The controller 110 may control the power/RF generator 120 to provide an output signal that may be used to perform a procedure on a patient. The feedback circuit 130 may provide feedback information (e.g., voltage, current, temperature, etc.) to the controller 110. The controller 110 may adjust the power/RF generator 120 to modify the output signal based on the feedback information. In some examples, the medical device 100 may be configured to perform tissue ablations.

In general, control of the medical device 100 may be achieved through some combination of temperature feedback and impedance feedback (load curves). Load curves used in the medical device 100 may define how much power to deliver to tissue at a particular impedance. These load curves typically are controlled based on current, voltage, power, impedance or combinations thereof. During an ablation, in a constant power application, the controller 110 may set current and voltage limits, which may define a power operating envelope.

During a tissue ablation procedure, the medical device 100 may be configured to produce very high output voltages capable of creating arcs between a probe attached to the medical device 100 and the patient. In some electrosurgical applications, arcs are highly desirable, as they effectively reduce the surface area of the electrode, increasing the current density, and producing desirable tissue effects which would be difficult or impossible to realize without arc formation. However, in tissue ablation applications, arcs may be undesirable. Specifically, the goal of diffusing heat uniformly over a relatively large ablation volume is confounded by arc formation. When arcs occur within an ablation target, small volumes of tissue adjacent to the electrode reach temperatures high enough to carbonize cellular matter, dramatically reducing thermal and electrical conductivity of said tissue, and limiting further heating of the ablation target. This is also true in some contact coagulation applications. Therefore, it can be highly advantageous to have a way to detect arcing. In some examples, the feedback circuit 130 may include circuitry capable of detecting a sudden drop in impedance, which is indicative of an arc. In another example, the feedback circuit 130 may be connected to an optical fiber cable that is inserted into the center of the probe and may detect an arc in response to detection of light. In response to detection of an arc, the feedback circuit 130 may provide a signal to the controller 110 and/or the power/RF generator 120 to shut off the output power or to redirect the output power to an internal load to extinguish the arc.

In some examples, ablation may be controlled by setting the power/RF generator 120 to a power output and applying power for a certain time period. Guidance is given to the operator as to power and time settings, but operators may use default power and time settings. This may result in ablations that are highly variable as the power output is highly dependent on the tissue impedance. Further, during an ablation, the tissue impedance may vary, starting with an initial low impedance followed by a small reduction in impedance. A sharp increase may indicate too much heat is being applied. Depending only on the power setting and the time setting, the ablation size can be highly variable, especially if the initial impedance is causing significant current limiting of the power. The current limit is often set independently from tissue impedance often based on component size limits or based off legacy designs. For many RF generators, current limiting occurs up to 50-100 ohms. Therefore, the medical device 100 may include circuitry that is configured to control an RF ablation with impedance control rather than timed control or temperature control for an ablation. In other words, the feedback circuit 130 may provide impedance information to the controller 110 based on the output signal and the controller 110 may adjust the power provided by the power/RF generator 120 in response to the impedance information.

In some examples, the power/RF generator 120 may include one or more RF generators that may be configured to output two different high frequency current signals. For example, in some instances, a single generator 120 may be configured to produce and output two high-frequency current signals. However, in other instances, multiple (e.g., two) generators 120 may be configured such that each generator produces a single high-frequency current signal (and combined they produce two high-frequency current signals).

Additionally, several hardware implementations may exist which would allow generation of high-frequency currents via the RF generators 1124 and 1126 with slightly different frequencies. An instrument having electrodes coupled to the two or more RF generators may attach to the patient and areas where the two or more current signals overlap or interfere with each other may result in a lower frequency current signal that is conducive to ablation in those areas (which may permit ablation in the sub-surface space 1054).

Further, in some instances, it may be desirable to increase the footprint (e.g., total volume) of tissue targeted by an RF ablation procedure and/or reduce the procedural time required to form an ablation. The power/RF generator 120 may increase the size of tissue targeted by RF ablation and/or reduce the time of an RF ablation by utilizing both high frequency current signals (e.g., which are believed to primarily conduct as displacement currents through cell membranes) and low frequency current signals (e.g., which are believed to primarily conduct through ionic extracellular fluid). The combination of low frequency current signals and high frequency current signals may effectively utilize both conduction modalities, increasing the size of an ablation target site that can be formed prior to loss of thermally and electrically conductive fluids. Several hardware implementations may be used for generation of both high-frequency and low-frequency signals from a single RF ablation generator. Example embodiments may include multi-resonant designs, filtered and un-filtered class-D inverters, and any number of other hardware realizations of this concept.

Inferential Heating

Heating tissue via thermal ablation is a common means of modifying tissue (e.g., eliminating tissue) for treatment of various diseases and conditions. In particular, the use of a radiofrequency (RF) current to cause heating of tissue is common, as it is easily controlled and conveniently applied. Numerous conditions exist that may benefit from ablative heating in tissue that is not accessible on the surface. For instance, accessing a tumor in a parenchymal organ (such as the liver) may require cutting into the organ, or inserting a needle electrode through the tissue to make electrical connection with the tumor. While the former is obviously invasive, the latter also carries risks (such as the "seeding" of malignant cells into previously-unaffected tissue as the needle is removed or repositioned). Other needs for subsurface ablation may be seen in dermatological applications: heating subcutaneous fat may cause cellular lysis and reabsorption or neocollagenesis, resulting in reduced appearance of wrinkles, cellulite, or scars. Neocollagenesis may non-ablatively remodel tissue. For example, it may be desirable to heat tissue to 40-50 C to cause neocollagenesis (rather than to 50-100 C which may cause tissue destruction).

In yet other examples, it may be undesirable to incise or puncture the skin to access the subcutaneous space. Therefore, it can be appreciated that a need exists for heating (or ablation) of inaccessible subsurface tissues without damaging or affecting the surface tissue. This disclosure includes embodiments of a system and methods for achieving ablations (e.g., sub-surface ablations) using interferential heating, whereby inferential heating may then be utilized to treat a variety of conditions, such as the treatment of inaccessible subsurface tissues.

In some examples, inferential heating methodologies may include two or more pairs of electrodes attached to the surface of tissue whereby multiple high-frequency currents are passed (e.g., flow) between the electrode pairs. Further, at certain locations these multiple high-frequency currents interfere (e.g., overlap) with one another thereby creating a "low-frequency interferential current." This low-frequency interferential current may be greater in magnitude than one or both of the high-frequency currents, and therefore, may produce sub-surface heating at a rate that exceeds surface heating at the tissue-electrode interface. Additionally, the low-frequency interferential current may also be greater in magnitude than the magnitude of two currents of the same frequency which overlap without generation of interferential current.

Figure 2:
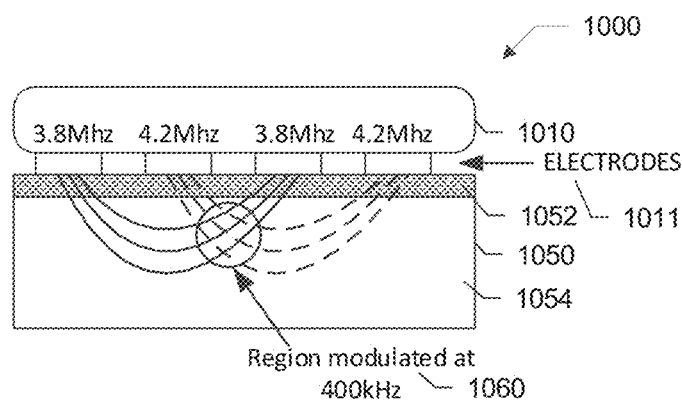
FIG. 2 depicts an example of an interferential heating medical system in accordance with an embodiment of the disclosure.

FIG. 2 depicts an example of an interferential heating medical system 1000 in accordance with an embodiment of the disclosure. The interferential heating medical system 1000 includes an instrument 1010 with electrodes 1011 coupled between the instrument 1010 and the skin layer (e.g., epidermis) 1052 of the tissue 1050. A first pair of the electrodes 1011 are configured to provide a 3.8 MHz signal and a second pair of the electrodes 1011 are configured to provide a 4.2 MHz signal (e.g., two high-frequency currents). The lines extending from the electrodes 1011 into the skin layer 1052 and into the sub-surface area of the tissue 1050 represent the flow of the electrical currents. The high-frequency signals alone may penetrate the skin layer 1052, whereas a low-frequency signal would heat the surface of the skin. However, in the sub-surface area 1060 where the two currents interfere, the interference between the currents results in modulation at 400 kHz, which is sufficient to perform tissue ablation.

Figure 3:
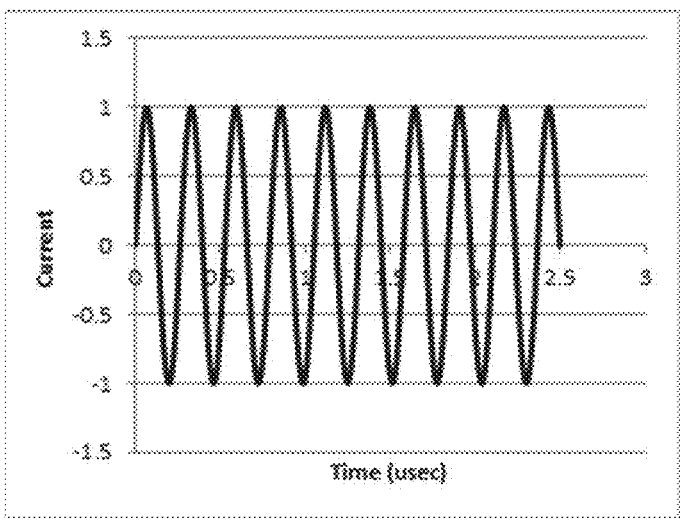
FIG. 3 is an illustration of a graph showing only high frequency current signals in accordance with an embodiment of the disclosure.
Figure 4:
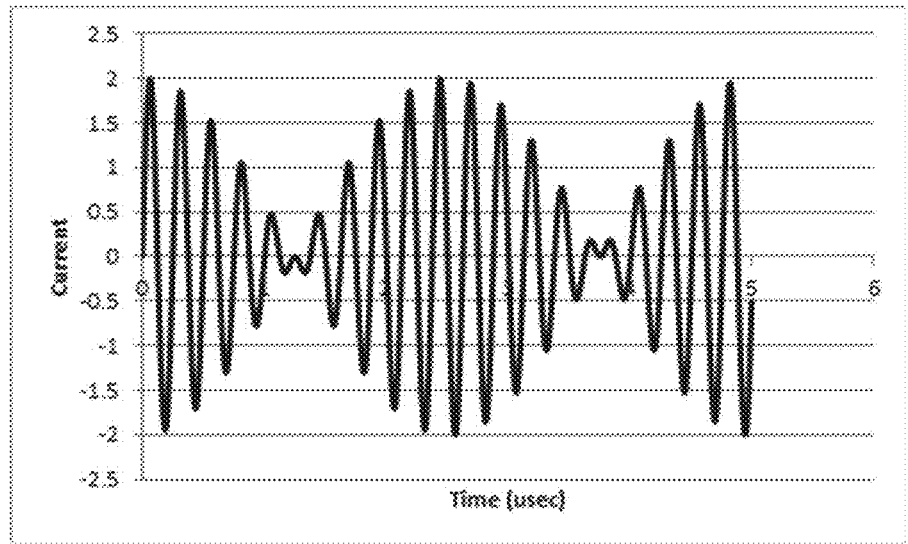
FIG. 4 is an illustration of a graph showing current in the sub-surface region 1054 having current signals at a higher amplitude in accordance with an embodiment of the disclosure.

FIG. 3 is an illustration 1001 of a graph showing only high-frequency current signals in accordance with an embodiment of the disclosure. FIG. 4 is an illustration 1002 of a graph showing an inferential current in the sub-surface region 1054 having low-frequency current signals at a higher amplitude in accordance with an embodiment of the disclosure. It is noted that the 3.8 MHz, 4.2 MHz, and 400 kHz frequencies described herein are merely exemplary, and other frequencies may be used without departing from the scope of the disclosure. For example, the individual high-frequency signals described above may include radio frequency currents in the range of about 750 kHz to 20 MHz, or in the range of about 500 kHz to 20 MHz, or in the range of about 1 MHz to about 10 MHz, or in the range of about 2 MHz to about 5 MHz. Generally, the sub-surface modulated signal (e.g., the inferential ablation current) may include low-frequency currents in the range of about 50 kHz and 1 MHz, or in the range of about 200 kHz to about 800 kHz.

Figure 5:
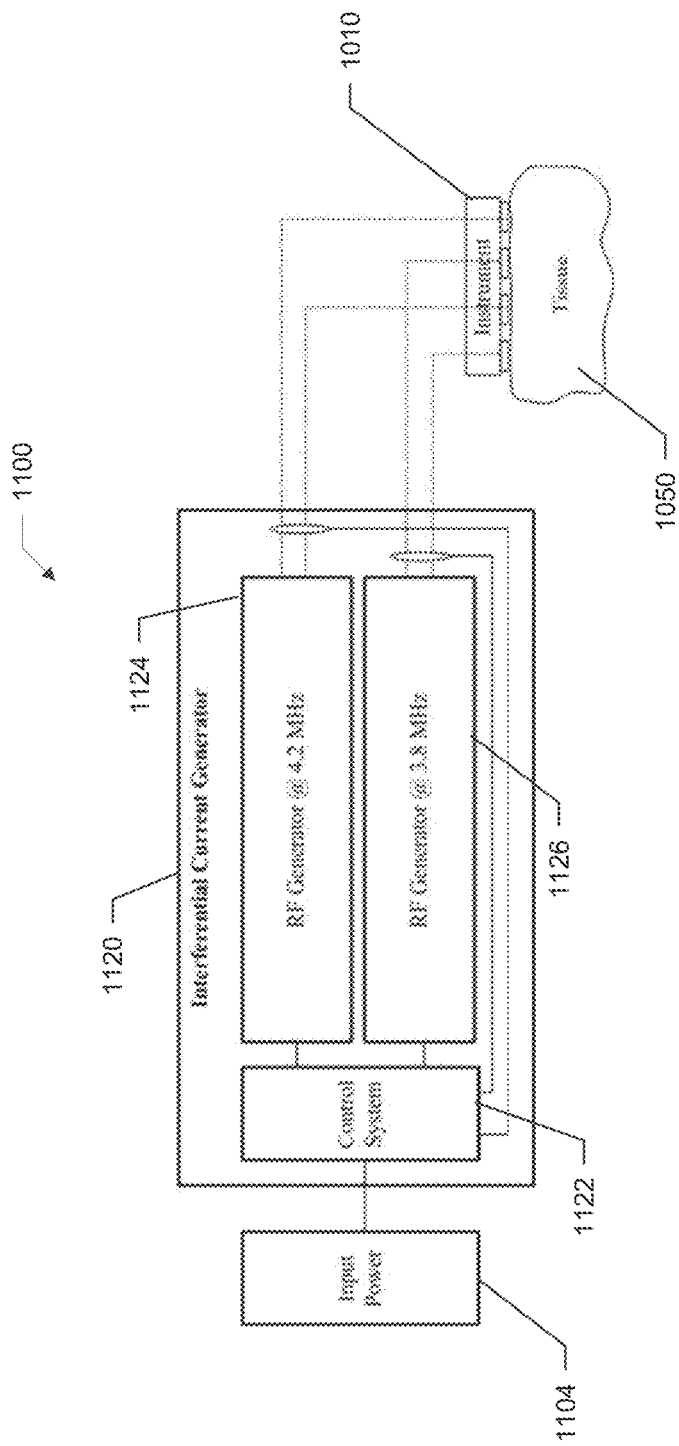
FIG. 5 depicts an example medical device for interferential heating in accordance with an embodiment of the disclosure.

FIG. 5 illustrates an example medical device 1100 which may be utilized for interferential heating in accordance with an embodiment of the disclosure. The medical device 1100 may be implemented in the medical device 100 of FIG. 1. The medical device 1100 may include elements that have been previously described with respect to the interferential heating medical system 1000 of FIG. 2. Those elements have been identified in FIG. 5 using the same reference numbers used in FIG. 2 and operation of the common elements is as previously described.

The medical device 1100 may include an input power source 1104, an interferential RF current generator 1120 and an instrument 1010 (e.g., an instrument including one or more pairs of electrodes as described above) connected to tissue 1050. The interferential RF current generator 1120 may include a control system 1122 and an RF generator. FIG. 5 illustrates two RF generators 1124 and 1126, each of which are utilized to produce a single high-frequency signal (e.g., each generator outputs a single high-frequency signal). However, this is not intended to be limiting. Rather, it is contemplated that a single RF generator may be utilized to generate and output multiple, different high-frequency signals.

As shown in FIG. 5, the RF generator 1124 may generate the 4.2 MHz current signal and the RF generator 1126 may generate the 3.8 MHz current signal. Several hardware implementations may exist which would allow generation of high-frequency currents via the RF generators 1124 and 1126 with slightly different frequencies. These may include multi-resonant inverters, de-tuned tank circuits, or simply multiple inverters (of any type) placed inside a common enclosure As shown in the instrument 1010, the electrode connections for the two the RF generators 124 and 126 may alternate such that there is an overlapping (e.g., interference) area within the tissue where two high-frequency currents may interfere with each other to create a lower-frequency current that can be used to perform a sub-surface ablation procedure. The magnitude of the interferential current generated in such a system results in a low-frequency current which is greater in magnitude than would be realized in a system where the two RF generators realize an increased sub-surface current through simple addition. An interferential system utilizing two RF generator current signals at different frequencies, as previously described, will realize a sub-surface current which is greater in magnitude than the sum of the currents produced by the individual generators. Furthermore, since tissue heating is proportional to the square of the ablation current, the resulting tissue heating using an interferential current is exponentially higher than a non-interferential system.

Several end effector electrode configurations implemented in the instrument 1010 may exist that would allow application of the interferential currents. It is imagined that different configurations will exist for different therapies, diseases, and tissue types, but that end effectors will generally consist of multiple pairs of electrodes arranged in a geometric configuration. While the ideal embodiment of the end effector may allow non-traumatic application to a surface, other embodiments may consist of penetrative (e.g., needle) electrodes.

In some examples, a system and method for generating interferential currents in tissue produce an ablation effect. In other words, the interferential ablation currents may be defined as a low-frequency current which heats targeted tissue to a desired degree (e.g., to a level which potentially destroys the tissue). In other examples, the heating may not be sufficient to irreversibly damage or destroy tissue, but merely sufficient to cause desirable effects such as remodeling. In some examples, the ratio of sub-surface heating to surface heating is higher than that of a system containing only a single-frequency current source. The high-frequency currents may generally fall in the range of about 750 kHz to 20 MHz, or in the range of about 500 kHz to 20 MHz, or in the range of about 1 MHz to about 10 MHz, or in the range of about 2 MHz to about 5 MHz and may be selected to minimize heating of the tissue-electrode interface. The interferential currents may be realized due to the difference in frequency between the high-frequency currents and may be selected to maximize sub-surface heating. The area where the two high frequency currents overlap may exponentially increase the high frequency current heating. Generally, the sub-surface modulated signal (e.g., the inferential ablation current) may include low-frequency currents in the range of about 50 kHz and 1 MHz, or in the range of about 200 kHz to about 800 kHz.

An example medical device may include an interferential RF current generator that produces two or more therapeutic high-frequency currents whose frequency differs by an amount selected to produce a lower-frequency interferential current when the high-frequency currents flow in the same conductive tissue region. For example, a medical device for ablating tissue may utilize a radio frequency generator to apply a first radio frequency current having a frequency at or above 1 MHz to a target tissue, and apply a second radio frequency current having a frequency at or above 1 MHz that is different from the frequency of the first radio frequency current to the target tissue such that the second radio frequency current interferes with the first radio frequency current to generate an interferential ablation current within the target tissue.

Additionally, it can be appreciated that any of the medical devices (e.g., systems) described herein may include an end effector designed to deliver an interferential current to tissue. The end effector may include multiple pairs of electrodes intended to conduct one or more high-frequency currents. In some examples, the end effector may rely on capacitive coupling of energy to tissue, rather than ohmic conduction. The configuration of electrodes on the end effector may create a spatial region where interferential currents may be generated due to the conduction of two or more high-frequency currents in the same tissue.

Multi-Frequency Heating

Multi-frequency heating is another example method which may improve RF ablation systems. A typical RF ablation procedure may involve a surgeon positioning an electrode (e.g., often a needle) into (or adjacent to) an ablation tissue target, potentially using ultrasound or fluoroscopic imaging guidance. The electrode may be connected to an RF power supply (e.g., a RF power generator as described above) with the electrical circuit completed via a large return electrode plate positioned on the patient. During the procedure, RF current may be allowed to flow for a length of time, after which it is assumed that sufficient heating has occurred to ablate the target tissue. While some RF ablation systems may contain temperature sensors and control systems to regulate temperature at the ablation target to a prescribed value, it is generally difficult to assess efficacy of the ablation in real-time. Practitioners rely on "recipes" for time and temperature which have previously been shown to be effective in particular clinical situations.

In many clinical situations, larger and/or faster ablations are desired which in some cases may be provided by a single electrode. As the electrode heats the tissue, the tissue adjacent to the needle may become dehydrated. As fluid is the primary electrical and thermal conductor in tissue, the loss of fluid results in the cells conducting less electrical current and conducting less heat flux. Specifically, some existing RF ablation power supplies produce a single frequency output, typically around 500 kHz. It is believed that such a frequency primarily heats extracellular fluids (e.g., primarily ionized water), which then heats intracellular contents via thermal conduction. As extracellular fluid is heated and displaced, the ability to heat intracellular contents becomes limited as the electrode no longer has an efficient means to conduct current into the tissue. Accordingly, there is a physical limit to the size (e.g., the total volume and/or amount) of target tissue that can be ablated with a single electrode. In other words, as the ablation zone begins to form, it self-limits to a particular size and no amount of additional power or time will result in a markedly larger volume of tissue which is ablated. The amount (e.g., total volume) of target tissue which is ablated is often much smaller than desired for clinical effectiveness.

One method of overcoming this fundamental limit on the size of RF ablations may include use of multiple electrodes (e.g., multiple needle electrodes). However, the use of multiple ablation electrodes is a non-ideal solution as it requires careful placement of multiple electrodes and cannot necessarily be configured to produce the desired ablation size/shape. Another method for better control of ablation size/shape may include use of microwave energy, rather than RF current. Microwave energy heats tissue via a different mechanism that is less affected by dehydration of tissue adjacent to the electrode. However, microwave ablation may require special "antenna" electrodes, more careful pre-procedural-planning and different safety considerations. Aside from the different heating mechanism used in microwave ablation, different frequency RF currents take different electrical paths through tissue. That is, higher frequencies may conduct through the small capacitances formed across cellular membranes, resulting in currents flowing through the intracellular matter, directly heating it (e.g., rather than indirectly through thermal conduction). Thus, a higher frequency may heat tissue through a different physical mechanism than a lower frequency. Therefore, in some instances it may be desirable to combine the beneficial heating properties of both high-frequency heating and low-frequency heating to effectively ablate tissue.

In some instances, combining the beneficial heating properties of both high-frequency heating and low-frequency heating may permit larger ablations using RF. Increasing the size of RF ablations would offer numerous potential benefits, such as: 1) increased confidence that the target tissue was fully ablated, 2) ease in precise positioning of the electrode, 3) increased procedural efficacy, as larger ablations minimize the impact of random variabilities in tissue properties that may make an ablation insufficient (despite using the correct "recipe") and, 4) quicker, less invasive procedures, as less time and fewer electrodes may be used to produce the same, large, ablation, or combinations thereof.

Some example methods include RF ablation of tissue by applying both high frequencies (e.g., which are believed to primarily conduct as displacement currents through cell membranes) and lower frequencies (e.g., which are believed to primarily conduct through ionic extracellular fluid). Some examples described herein may include a method for increasing the size of an RF ablation by using both high frequencies (e.g., which are believed to primarily conduct as displacement currents through cell membranes) and lower frequencies (e.g., which are believed to primarily conduct through ionic extracellular fluid). This combination may effectively utilize both conduction modalities to heat and/or ablate target tissue, in some cases effectively increasing the size of an ablation that can be formed prior to the loss of thermally and electrically conductive fluids.

Figure 6:
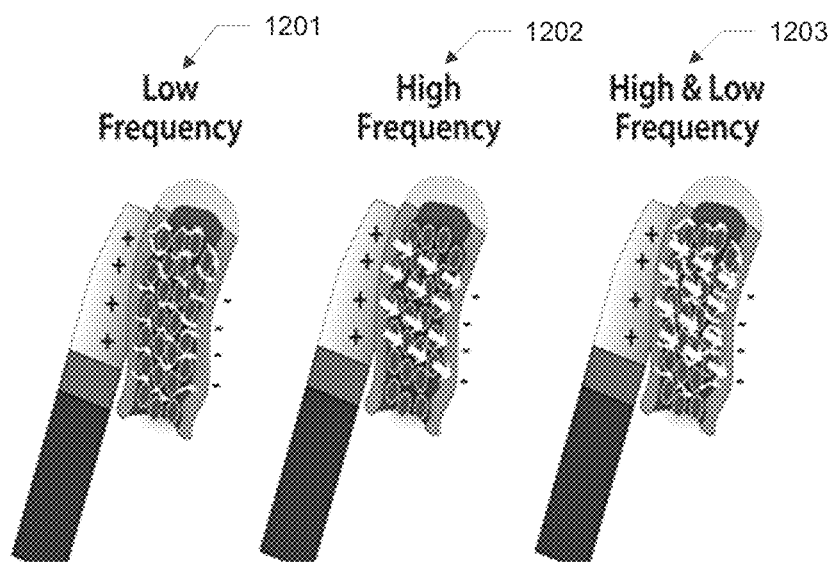
FIG. 6 includes illustrations of pathways for electrical currents through tissue in accordance with an embodiment of the disclosure.

The medical device 100 of FIG. 1 may implement a power/RF generator 120 to generate and utilize both high and low frequencies to ablate (e.g., to heat and possibly destroy) a target tissue site. FIG. 6 includes illustrations 1201, 1202, and 1203 which illustrate example pathways for electrical ablation currents passing through tissue in accordance with embodiments disclosed herein. For purposes of discussion herein, an ablation current may include an electrical current that includes enough energy to effectively ablate (e.g., to heat and possibly destroy) a targeted tissue site. For example, the first illustration 1201 depicts a low frequency ablation current pathway through ionic extracellular fluid. The second illustration 1202 depicts a high frequency ablation current pathway acting as displacement current through cell membranes. The third illustration 1203 shows the simultaneous combination of the low and high frequency ablation current pathways of the first and second ablation current pathways shown in illustrations 1201 and 1202, respectively.

It can be appreciated that, in at least some examples, the high-frequency ablation current and low-frequency ablation current may be transmitted (e.g., delivered) to a target tissue site along the same conductive pathway. In other examples, however, the high-frequency ablation current and low-frequency ablation current may be transmitted (e.g., delivered) to a target tissue site along the different conductive pathways. Furthermore, it can be appreciated that, in at least some examples, the high-frequency ablation current and low-frequency ablation current may be electrically transmitted (e.g., delivered) via the same electrode. In other words, in some examples, the high-frequency ablation current and low-frequency ablation current may be generated by a single point electrode and follow the same electrical pathway when ablating a target tissue site. However, in other examples, the high-frequency ablation current and low-frequency ablation current may be generated by multiple electrode pairs when ablating a target tissue site. For example, the high-frequency current may be generated by a first pair of electrodes and the low-frequency current may be generated by a second pair of electrodes. Further, multiple pairs of electrodes may be utilized to generate any of the current disclosed herein. Additionally, any of the electrodes described herein (e.g., the single electrode and/or any electrode pair) utilized to generate the high-frequency ablation current and/or the low-frequency ablation current may operate in either a monopolar or bipolar configuration.

Figure 7:
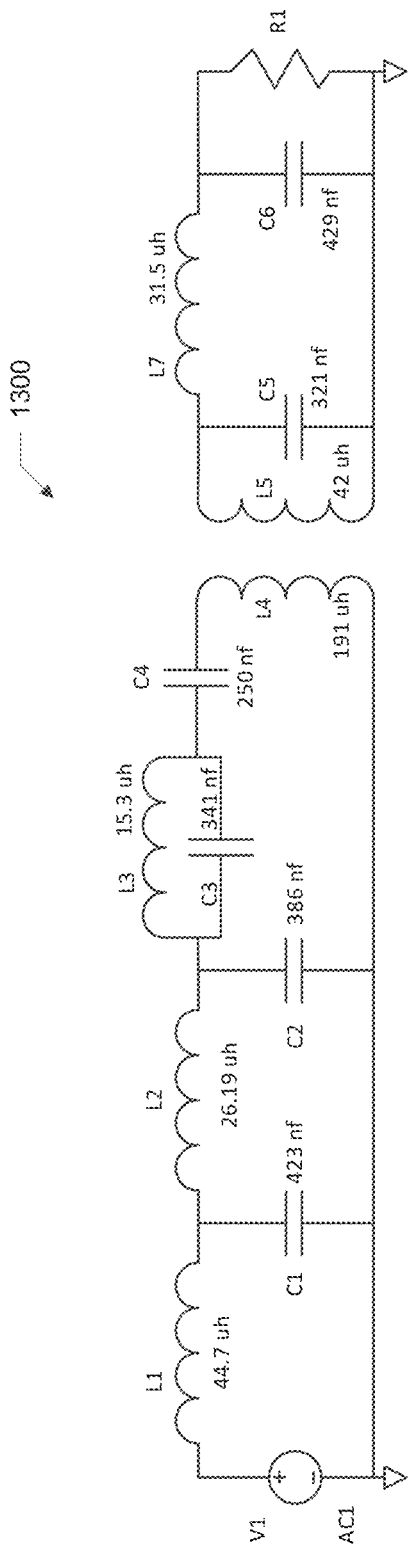
FIG. 7 depicts an exemplary LC ladder circuit having a multi-resonant output in accordance with an embodiment of the disclosure.
Figure 8:
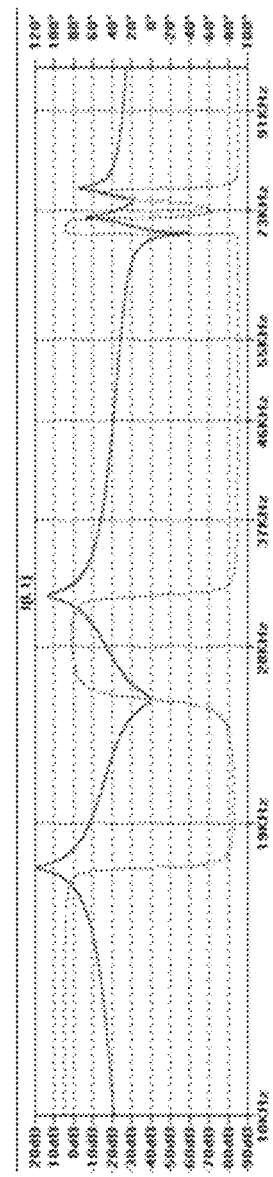
FIG. 8 depicts a frequency response of the LC ladder circuit of FIG. 7.

Several hardware implementations may be used for the generation of both the high-frequency and low-frequency signals from the single RF ablation generator 120. Example embodiments may include multi-resonant designs, filtered and un-filtered class-D inverters, and any number of other hardware realizations of this concept. FIG. 7 depicts an exemplary LC ladder circuit 1300 having a multi-resonant output in accordance with an embodiment of the disclosure. FIG. 8 depicts a frequency response 1301 of the LC ladder circuit 1300 of FIG. 7. The LC ladder circuit 1300 may be implemented in the power/RF generator 120 of FIG. 1.

Figure 9:
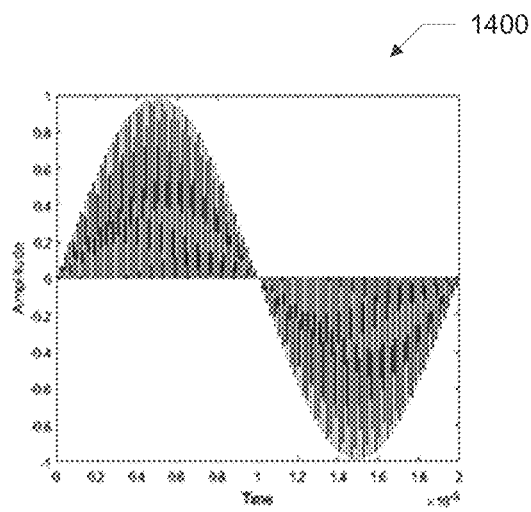
FIG. 9 depicts an example electrical waveform where the envelope of a signal is modulated at a low frequency while the signal itself is modulated at a high frequency in accordance with an embodiment of the disclosure.
Figure 10:
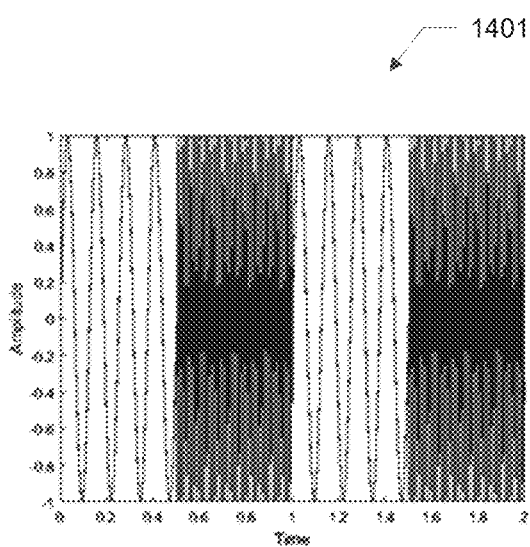
FIG. 10 illustrates another example electrical waveform where the low frequency signal is time-multiplexed with delivery of a high frequency signal, resulting in the signals being delivered sequentially, in accordance with an embodiment of the disclosure.

Production of high-frequency and low-frequency ablation currents may be accomplished in numerous ways. FIG. 9 depicts an example electrical waveform 1401 where the envelope of a signal is modulated at a low frequency (e.g., at approximately 200 kHz) while the signal itself is modulated at a high frequency (e.g., approximately 2 MHz) in accordance with an embodiment of the disclosure. Accordingly, the high and low frequencies are delivered to the target tissue simultaneously. In other examples, such as that depicted in FIG. 10, an example electrical waveform 1402 where the low frequency (e.g., 200 kHz) signal is time-multiplexed with the delivery of a high-frequency (e.g., 2 MHz) signal, thereby resulting in the high-frequency signal and the low-frequency signal being delivered sequentially with one another in accordance with an embodiment of the disclosure. It can be appreciated that numerous permutations of these types of delivery methods may exist without departing from the scope of the disclosure. For instance, in some examples, either the high-frequency and/or low-frequency ablation currents may be applied directly before or directly after one another. In other examples, at least a portion of either the high-frequency and/or low-frequency ablation currents may interfere (e.g., overlap) with a portion of the other.

Additionally, when the high-frequency and low-frequency signals are delivered in sequence, the relative amount of time each signal is transmitted may be adjusted to optimize the desired effect on the target tissue. For example, the relative amount of time the high-frequency and low-frequency signals are transmitted may be adjusted to any ratio. In some examples, the low-frequency signals may be transmitted over a longer time period relative to the high-frequency signals. In other examples, the high-frequency signals may be transmitted over a longer time period relative to the low-frequency signals. Additionally, the absolute length of each segment may also be varied as one accounts for the time-dependent thermal properties of different tissue types (e.g. 1 ms/1 ms, 200 ms/50 ms, etc.).

In some examples, a high-frequency radio frequency ablation current may be applied over a first time period at a first power level and the low-frequency radio frequency ablation current may be applied over a second time period at a second power level, whereby each of the first power level and the second power level are sufficiently high to ablate the target tissue site. Further, the first time period may be different from the second time period. Additionally, in some instances, at least a portion of the first time period may overlap with at least a portion of the second time period. Further yet, in some examples, the second time period may occur immediately after the first time period, and in other examples the entire second time period may occur simultaneously within the first time period.

As discussed above, in some examples, the medical device 100 may, simultaneously, utilize both high-frequency and low-frequency ablation currents, which may, for example, increase the total volume of target tissue ablated. Further, simultaneous application of both high-frequency and low-frequency electrical currents may decrease the time of a tissue ablation procedure.

In some examples, the simultaneous application (e.g., delivery, transmission) of one or more high-frequency signal(s) and one or more low frequency signals may include one or more high-frequency signal(s) that may be adapted and/or configured to primarily directly heat intracellular matter (e.g., rather than indirectly through thermal conduction), and the one or more low-frequency signal(s) may be configured to primarily heat extracellular fluids, which then heats intracellular contents via thermal conduction. In some examples, the simultaneous application (e.g., delivery, transmission) of high-frequency signal and low frequency signal may include one or more high-frequency signal in a range of 600 kHz to 10 MHz, or in a range of 600 kHz to 20 MHz, or in a range of 600 kHz to 30 MHz, or in the range of 750 kHz to 15 MHz, or in the range of 1 MHz or above; and one or more low-frequency signals in a range of 50 kHz to 550 kHz, or in the range of 50 kHz to 500 kHz, or in the range of 200 kHz to 500 kHz. Based on these frequency ranges, it can be appreciated that simultaneous application (e.g., delivery, transmission) of one or more low-frequency signal and one or more high-frequency signal may include a ratio of the low-frequency signal to the high-frequency signal to be in the range of 1:2 to 1:400, for example, in the range of 1:2 to 1:200, for example, in the range of 1:4 to 1:200, for example, in the range of 1:4 to 1:400, for example, in the range of 1:2 to 1:50, or for example in the range of 1:3 to 1:25. However, it is contemplated that any ratio of the low-frequency signal to the high-frequency signal may be utilized during the simultaneous application (e.g., delivery, transmission) of both the low-frequency and high-frequency signals. In some cases, the actual difference in frequency between the high frequency signal and the low frequency signal may be 500 kHz or more, 750 kHz or more, 1 MHz or more, or in some examples, 2 MHz or more.

As described above, it can be appreciated that an example method for ablating tissue may include applying a first radio frequency ablation current to a target tissue and applying a second radio frequency ablation current to the target tissue, wherein the ratio of the frequency of the first radio frequency ablation current to the second radio frequency ablation current is in the range of 1:2 to 1:400. In some instances, the low-frequency signal and the high-frequency signal which are applied simultaneously to a target tissue site may be chosen to heat both intra-cellular and extra-cellular tissue matter. The extracellular tissue matter may be preferentially heated by low-frequency ablation currents that flow through conductive fluids surrounding the target tissue cells. The intracellular tissue matter may be preferentially heated by high-frequency ablation currents that access the intracellular space by conduction through capacitances formed by cellular membranes.

Additionally, the power may be delivered to the target tissue at two or more frequencies such that the size of the targeted ablation area is maximized. In some examples, the average power delivered is generally in the range of 1 to 300 W. As discussed above, the delivery (e.g., application, transmission) of the high-frequency and low-frequency ablation currents may be either simultaneous or sequential. When the delivery of the high-frequency and low-frequency currents are simultaneous, the envelope of the signal may be adjustable. When the delivery of the high-frequency and low-frequency currents is sequential, the absolute time spent conducting either the high-frequency current, the low-frequency current, or no current may be adjustable.

An end effector (electrode) may be designed to permit conduction of said currents through living tissue. The end effector may contain provisions for monitoring the temperature of the tissue directly in contact with the end effector. The end effector may contain multiple electrical connection points to mechanically increase the region of tissue in which current flows. As discussed above, the example medical device 100 may include an RF power supply ("generator") that is electrically connected to the end effector and implements the prescribed method for delivery of low-frequency and high-frequency ablation currents.

What is claimed is:

1. A method for ablating tissue, the method comprising:
   emitting a first radio frequency ablation current from a first electrode to ablate a target tissue;
   emitting a second radio frequency ablation current from a second electrode to ablate the target tissue;
   directly heating extracellular matter of the target tissue by the emitted first radio frequency ablation current; and
   directly heating intracellular matter of the target tissue by the emitted second radio frequency ablation current;
   wherein the ratio of the frequency of the first radio frequency ablation current emitted from the first electrode to the second radio frequency ablation current emitted from the second electrode is in the range of 1:4 to 1:400;
   wherein the first radio frequency ablation current emitted from the first electrode is in the range of 50 kHz to 550 kHz;
   wherein the second radio frequency ablation current emitted from the second electrode is in the range of 600 kHz to 10,000 kHz.

2. The method of claim 1, wherein the first radio frequency ablation current and the second radio frequency ablation current are applied simultaneously to the target tissue.

3. The method of claim 1, wherein the first radio frequency ablation current and the second radio frequency ablation current are applied in sequence to the target tissue.

4. The method of claim 1, wherein the first radio frequency ablation current is configured to directly heat through a first current path, and wherein the second radio frequency ablation current is configured to directly heat through a second current path.

5. The method of claim 1, wherein the first radio frequency ablation current and the second radio frequency ablation current are configured to maximize the total volume of target tissue to be ablated.

6. The method of claim 1, wherein the first radio frequency ablation current is applied over a first time period at a first power level and the second radio frequency is applied over a second time period at a second power level, and wherein each of the first power level and the second power level are sufficiently high to ablate the target tissue site.

7. The method of claim 6, wherein the first time period is different from the second time period.

8. The method of claim 6, wherein at least a portion of the first time period overlaps with at least a portion of the second time period.

9. The method of claim 6, wherein the second time period occurs immediately after the first time period.

10. The method of claim 6, wherein the entire second time period occurs simultaneously within the first time period.

11. The method of claim 1, wherein the first radio frequency ablation current and the second radio frequency ablation current are transmitted along the same electrical pathway.

12. The method of claim 1, wherein the first radio frequency ablation current and the second radio frequency ablation current are generated between the first electrode and the second electrode, and wherein the first electrode and the second electrode operate in a monopolar arrangement.

13. The method of claim 1, wherein the first radio frequency ablation current and the second radio frequency ablation current are generated between the first electrode and the second electrode, and wherein the first electrode and the second electrode operate in a bipolar arrangement.

14. A method for ablating tissue, the method comprising:
applying a first radio frequency ablation current to ablate a target tissue site through a first electrode; and
applying a second radio frequency ablation current to ablate the target tissue site through a second electrode;
directly heating extracellular matter of the target tissue by the emitted first radio frequency ablation current; and
directly heating intracellular matter of the target tissue by the emitted second radio frequency ablation current;
wherein the second radio frequency ablation current has a higher frequency than the first radio frequency ablation current;
wherein the first radio frequency ablation current is configured to directly heat through a first current path, and wherein the second radio frequency ablation current is configured to directly heat through a second current path;
wherein the ratio of the frequency of the first radio frequency ablation current to the second radio frequency ablation current is in the range of 1:4 to 1:400;
wherein the first radio frequency ablation current applied through the first electrode is in the range of 50 kHz to 550 kHz;
wherein the second radio frequency ablation current applied through the second electrode is in the range of 600 kHz to 10,000 kHz.

15. The method of claim 14, wherein the first radio frequency ablation current and the second radio frequency ablation current are applied simultaneously to the target tissue site.

16. The method of claim 14, wherein the first radio frequency ablation current and the second radio frequency ablation current are applied in sequence to the target tissue site.

17. The method of claim 14, wherein the first radio frequency ablation current and the second radio frequency ablation current are configured to maximize the total volume of target tissue to be ablated.

18. The method of claim 14, wherein the first radio frequency ablation current is applied over a first time period at a first power level and the second radio frequency is applied over a second time period at a second power level, and wherein each of the first power level and the second power level are sufficiently high to ablate the target tissue site.

19. The method of claim 18, wherein the first time period is different from the second time period.

20. The method of claim 18, wherein at least a portion of the first time period overlaps with at least a portion of the second time period.

21. The method of claim 18, wherein the second time period occurs immediately after the first time period.

22. The method of claim 18, wherein the entire second time period occurs simultaneously within the first time period.

23. A medical device for ablating tissue, the device comprising:
a radio frequency generator configured to provide a first radio frequency ablation current to ablate a target tissue and a second radio frequency ablation current to ablate the target tissue; and
wherein the first radio frequency ablation current is emitted from a first pair of electrodes to ablate the target tissue;
wherein the second radio frequency ablation current is emitted from a second pair of electrodes to ablate the target tissue;
wherein the first radio frequency ablation current emitted from the first pair of electrodes is configured to directly heat extracellular matter of the target tissue;
wherein the second radio frequency ablation current emitted from the second pair of electrodes is configured to directly heat intracellular matter of the target tissue;
wherein the ratio of the frequency of the first radio frequency ablation current to the second radio frequency ablation current is in the range of 1:4 to 1:400;
wherein the first radio frequency ablation current emitted from the first pair of electrodes is in the range of 50 kHz to 550 kHz;
wherein the second radio frequency ablation current emitted from the second pair of electrodes is in the range of 600 kHz to 10,000 kHz.

24. The device of claim 23, wherein the device is configured to apply the first radio frequency ablation current and the second radio frequency ablation current simultaneously to the target tissue.

25. The device of claim 24, wherein the first radio frequency ablation current is configured to target extracellular matter, and wherein the second radio frequency ablation current is configured to target intracellular matter, or wherein the first radio frequency ablation current is configured to directly heat through a first current path, and wherein the second radio frequency ablation current is configured to directly heat through a second current path.

* * * * *